United States Patent
Hoffman et al.

(12)

(10) Patent No.: US 6,180,617 B1
(45) Date of Patent: *Jan. 30, 2001

(54) METHOD FOR REDUCING ABSORPTION OF UNDESIRED LIPIDS IN THE GASTROINTESTINAL TRACT

(76) Inventors: Allan S. Hoffman, 4528 Laurel Dr. NE., Seattle, WA (US) 98105; N. S. Choi, P.O. Box 10 - Dae Duk Dan Ji, Chung Nam (KR)

( * ) Notice: Under 35 U.S.C. 154(b), the term of this patent shall be extended for 0 days.

This patent is subject to a terminal disclaimer.

(21) Appl. No.: 08/485,092

(22) Filed: Jun. 7, 1995

Related U.S. Application Data

(63) Continuation of application No. 08/234,719, filed on Apr. 28, 1994, now Pat. No. 5,597,810, which is a continuation of application No. 07/888,396, filed on May 20, 1992, now abandoned, which is a continuation of application No. 07/609,013, filed on Oct. 30, 1990, now abandoned, which is a continuation of application No. 07/497,752, filed on Mar. 20, 1990, now abandoned, which is a continuation of application No. 07/382,042, filed on Jul. 18, 1989, now abandoned, which is a continuation of application No. 07/266,217, filed on Oct. 28, 1988, now abandoned, which is a continuation of application No. 07/136,476, filed on Dec. 23, 1987, now abandoned, which is a continuation of application No. 06/686,844, filed on Dec. 27, 1984, now abandoned.

(51) Int. Cl.$^7$ ................................................ A61K 31/70
(52) U.S. Cl. ................................ 514/54; 514/55; 514/57; 514/167; 514/762
(58) Field of Search .......................... 514/34, 55, 57, 514/167, 762

(56) References Cited

U.S. PATENT DOCUMENTS

| | | | |
|---|---|---|---|
| 2,962,419 | 11/1960 | Minich | 514/54 |
| 3,081,226 | 3/1963 | Di Luzio | 514/54 |
| 3,148,114 | 9/1964 | Fahrenbach et al. | 514/53 |
| 3,308,020 | 3/1967 | Wolf et al. | 514/23 |
| 3,415,927 | 12/1968 | Butensky et al. | 514/54 |
| 3,511,910 | 5/1970 | Halleck | 514/53 |
| 3,627,872 | 12/1971 | Parkinson | 514/57 |
| 3,849,554 | 11/1974 | Winitz | 514/53 |
| 3,851,057 | 11/1974 | Kuzuya | 514/54 |
| 3,856,945 | 12/1974 | Sugiyama et al. | 424/195.1 |
| 3,934,007 | 1/1976 | Gussin et al. | 424/125 |
| 3,954,976 | 5/1976 | Mattson et al. | 514/23 |
| 3,957,976 | 5/1976 | Sugimoto | 514/53 |
| 4,005,195 | 1/1977 | Jandacek | 514/23 |
| 4,039,659 | 8/1977 | Gordon et al. | 424/115 |
| 4,058,601 | 11/1977 | Hata et al. | 514/51 |
| 4,076,930 | * 2/1978 | Ellingboe et al. | 536/1.1 |
| 4,175,124 | 11/1979 | Hyldon et al. | 514/54 |
| 4,223,023 | * 9/1980 | Furda | 536/2 |

OTHER PUBLICATIONS

Interaction of Proteins with Triton X–100–Substituted Sepharose 413, J. Nightingale Ju. 15, 1983

Hydrophobic Interaction Chromatography. J. Nightingale Journal of Chromatography, 101 (1974) 281–288.

Non–ionic Adsorptive Immobilization of Proteins to Palmityl–(1982) Substituted Sepharose 4B. J. Nightingale Euc. J. Biochem 601–610.

Performance of Hydrophobic Chromatography in Purification of Amylase Aug. 17, 1984. Chem. Eng. Dept. Kyoto University.

Enzyme Immobilization on Palmityl–Sepharose. J. Nightingale Dept. of Biochemistry, Michigan State University.

Pitha, Kociolek & Karon "Detergents Linked to Polysaccharides: Prepration & Effects on Membranes & Cells", J. Biochem. 9411 18(1979).

* cited by examiner

*Primary Examiner*—Elli Peselev
(74) *Attorney, Agent, or Firm*—Seed Intellectual Property Law Group PLLC

(57) ABSTRACT

A composition is disclosed for use in reducing the availability of undesired lipids, such as cholesterol, in the fluid media of the gastrointestinal tract prior to absorption of the lipids across the cells lining the tract. The composition is a nontoxic, substantially nondigestible polymer to which ligands are chemically bonded through biologically stable ether groups. The ligands scavenge the undesired lipids from the fluid media.

8 Claims, No Drawings

METHOD FOR REDUCING ABSORPTION OF UNDESIRED LIPIDS IN THE GASTROINTESTINAL TRACT

CROSS-REFERENCE TO RELATED APPLICATION

This application is a continuation of U.S. patent application Ser. No. 08/234,719, filed Apr. 28, 1994 now U.S. Pat. No. 5,597,810, which is a continuation of U.S. patent application Ser. No. 07/888,396, filed May 20, 1992, now abandoned, which is a continuation of U.S. Ser. No. 07/609,013, filed Oct. 30, 1990, now abandoned, which is a continuation of U.S. Ser. No. 07/497,752, filed Mar. 20, 1990, now abandoned, which is a continuation of U.S. Ser. No. 07/382,042, filed Jul. 18, 1989, now abandoned, which is a continuation of U.S. Ser. No. 07/266,217, filed Oct. 28, 1988, now abandoned, which is a continuation of U.S. Ser. No. 07/136,476, filed Dec. 23, 1987, now abandoned, which is a continuation of U.S. Ser. No. 06/686,844, filed Dec. 27, 1984, now abandoned.

TECHNICAL FIELD

This invention relates to a method for reducing the biologically active level of undesired lipids in the gastrointestinal tract and to novel compositions for use with the method.

BACKGROUND ART

The adverse effects of high plasma cholesterol have been extensively studied and a correlation has been described between plasma cholesterol and heart disease.

Numerous compositions have been proposed for controlling the amount of cholesterol present in the blood stream. Disclosed, for example, is use of certain nonfat esters as a fat substitute to control the intake of fat and the amount of lipids in the bloodstream (U.S. Pat. No. 2,962,419); administration of a special class of polysaccharides consisting of at least two glucopyronosic units, each linked to the other by a 1-3-glycosidic linkage (U.S. Pat. No. 3,081,226); oral administration of certain naturally occurring mucilaginous substances which exert a hypocholesteremic adjuvant action (U.S. Pat. No. 3,148,114); oral administration of non-toxic glycocholic acid-binding polymeric amines for binding bile acids in the gut (U.S. Pat. No. 3,308,020); oral administration of heat-modified guar gum (U.S. Pat. No. 3,415,927); incorporation of certain polysaccharide substances in food products (U.S. Pat. No. 3,511,910); oral administration of ether-type anion exchangers prepared from hydroxyl-containing polysaccharides and cross-linked polysaccharides containing amino, morpholino and guanidino basic functioning groups (U.S. Pat. No. 3,627,872); administration of a defined diet composition incorporating certain carbohydrates (U.S. Pat. No. 3,849,554); oral administration of diethylaminoethyl dextran (U.S. Pat. No. 3,851,057); oral administration of water-soluble konjac mannan (U.S. Pat. No. 3,856,945); oral administration of sucrose-containing sweeteners to which maltitol and/or lactitol is added (U.S. Pat. No. 3,957,976); use of liquid polyol fatty acid polyesters in combination with anti-anal leakage agents (U.S. Pat. No. 4,005,195); oral administration of Levorin (U.S. Pat. No. 4,039,659); and oral administration of oat or barley gum (U.S. Pat. No. 4,175,124).

DISCLOSURE OF INVENTION

Disclosed is a method of reducing the availability of undesired lipids, such as cholesterol, in the fluid media of the gastrointestinal tract prior to absorption of the lipids across the cells lining the tract. A novel composition is orally administered, the composition utilizing a nontoxic, substantially nondigestible polymer to which ligands are chemically bonded through biologically stable ether groups, the ligands attracting and scavenging undesired lipids from the fluid media of the gastrointestinal tract. The composition, with the scavenged lipids, is discharged from the gastrointestinal tract with the feces.

The invention provides a unique and effective way of reducing the availability of undesired lipids, prior to absorption of such lipids across the gastrointestinal mucosalcells, and prior to the lipids going into the lymph where it is deposited in the thoracic duct and enters the blood circulatory system at the juncture of the internal jugular and subclavian veins.

BEST MODE FOR CARRYING OUT THE INVENTION

The novel compositions described herein are employed for reducing the biologically active level of undesired lipids present in the gastrointestinal tract of animals prior to any substantial absorption of the lipids through the intestinal lining and into the bloodstream. The compositions are prepared by bonding ligands as pendant groups to nontoxic, substantially nondigestible polymers having multiple reactive hydroxyl groups thereon which form biologically stable ether linkages with the ligand. Polymers which may be employed include cellulose, cellulosic and modified cellulosic polymers, polysaccharides and synthetic polymers such as polyvinyl alcohol (PVA) and hydroxyethylmethacrylate (HEMA). In particular, alpha-cellulose, carboxymethylcellulose (CMC), hydroxypropylcellulose (HPC), hydroxypropylmethylcellulose (HPMC), hydroxyethylcellulose, algin, dextrose, pectin, agar, and chitin may be used. Combinations of different polymers and/or copolymers and mixed ligands may be employed. For example, cholesterol (as a ligand) and a hydrocarbon (as a ligand) may be attached to the backbone of a suitable polymer.

The ligand employed depends on the particular lipid to be removed. In general, the ligand should be substantially hydrophobic, capable of attracting and bonding, by secondary chemical forces, to the lipid desired to be removed, and capable of being bonded to the polymer through biologically stable ether groups. For example, the cholesterol molecule has a substantially planar shape. If cholesterol is desired to be removed, ligands having substantially straight-chain aliphatic groups ranging from 12 to 24 carbon atoms are capable of binding to cholesterol present in the gastrointestinal tract to hold it and prevent its absorption until the polymer to which the ligand is attached is discharged from the gastrointestinal tract. Cholesterol itself may also be used as a ligand, the cholesterol molecule bound to the polymer by (1) converting the single hydroxyl group of the cholesterol molecule to a reactive epoxy group for reaction with the polymer or (2) by use of an intermediate compound reactive with both the polymer and cholesterol or (3) by other suitable means. Other ligand substances which may be used include saturated and unsaturated alcohols which can be converted to epoxides by the addition and subsequent dehydrohalination of epichlorohydrin or by the use of other intermediate compounds reactive with both the polymer and cholesterol, such as 1,2-epoxyoctadecane, and butane diglycidylether, followed by reaction with lipid molecules having a group which may be bonded to the pendant epoxy group on the polymer backbone.

The percentage of ligand groups employed relative to the polymer may range widely from 1 to 50%, depending on the particular polymer used, the particular ligand employed, and the lipid to be removed.

Undesired lipids which can be removed using the compositions of this invention include cholesterol, and cholesterol esters, steroids, fat soluble drugs, fatty acids and fatty esters and their derivatives.

The lipids are attracted to and bound to the ligand by secondary chemical or VanderWaal's forces.

The compositions are used by oral administration The dosage will vary depending on the length of treatment and the condition being treated. Dosages can range from 0.1 gm/kg body weight to 5.0 gm/kg body weight. The compositions may be admixed with a carrier, such as a liquid or solid filler, diluent, food stuff etc. The carrier may comprise from 1 to 99% by weight of the total composition.

The following example illustrates preparation and use of compositions described above in reducing the level of undesired lipids, such as cholesterol, in the gastrointestinal tract of animals.

EXAMPLE 1

PREPARATION OF COMPOSITION

Hydroxypropylmethylcellulose (HPMC) containing 10% hydroxypropyl and 30% methoxyl groups with an average molecular weight of 86,000 was reacted with 2,3 epoxy n-propyl octadecyl ether, the reaction carried out in dioxane/methylene chloride solvent using stannic chloride as a catalyst for 48 hours. The reaction product was precipitated with hexane, filtered and washed repeatedly over a period of three days with acetone. After filtering, the product was dried in a vacuum oven for two days at about 40° C.

EXAMPLE 2

A special atherogenic diet having the following composition was fed to four groups of male Sprague Dawley rats, all very close to a specified weight of 350 gms. The composition of the atherogenic diet was as follows:

SPECIAL BASAL ATHEROGENIC DIET (SAD), Modified

| COMPOSITION | PERCENTAGE |
|---|---|
| Alphacel | 6.0% |
| Butterfat (Salt Free) | 40.0% |
| Cholesterol | 5.3% |
| Choline Dihydrogen Citrate | 0.4% |
| Salt Mixture W | 4.0% |
| Sucrose | 23.3% |
| Sodium Cholate | 2.0% |
| Vitamin Diet Fortification Mixture | 2.0% |
| Casein Purified High Nitrogen | 20.0% |

The animals, divided into four dietary groups, were fed the special atherogenic diet for one week to allow equilibration. The animals were then fed for 2½ weeks with 95% of the atherogenic diet plus 5% of a food additive—the food additive being hydroxylpropylmethylcellulose (HPMC) alone for Group II, HPMC reacted with 5% octadecyl glycidyl ether (ODGE) for Group III, and 5% HPMC reacted with 15% octadecyl glycidyl ether for Group IV. After 2½ weeks of consuming the special diet plus food additive, the animals were sacrificed and their plasma cholesterol levels measured. The results were as follows:

EFFECT OF FOOD ADDITIVE ON PLASMA CHOLESTEROL

| GROUP | DIET | CHOLESTEROL (mg/dl ± SEM) |
|---|---|---|
| I | SAD | 390 ± 23 (8 animals) |
| II | SAD + 5% (HPMC/5% ODGE) | 370 ± 45 (8 animals) |
| III | SAD + 5% (HPMC/15% ODGE) | 336 ± 17 (8 animals) |

A 14% reduction in mean plasma cholesterol level for the animals of Group III was noted compared with control Group I. The animals of Group III, incorporating the composition containing 5% octadecyl glycidyl ether bound to the modified cellulosic polymer, showed some improvement (Ca. 5%) in mean plasma cholesterol level over the control, although not as marked an improvement as the animals of Group III.

It is understood that this application is intended to cover any variations, uses or adaptations of the invention as may be considered to be known or customary practice in the art to which the invention pertains.

What is claimed is:

1. A method for effecting reduction of the biologically active level of an undesired lipid present in the fluid media of the gastrointestinal tract of humans or animals, said undesired lipid capable of being bound by a substantially straight-chain aliphatic group ranging from 12–24 carbon atoms, comprising:

orally administering therapeutically effective doses of a pharmaceutical composition containing a substantially water-soluble nondigestible polymer having multiple reactable hydroxyl groups, wherein said polymer is selected from the group consisting of cellulose polymers, algin, pectin, agar, chitin, polyvinyl alcohol and hydroxyethyl methacrylate, bonded through a biologically stable ether linkage to a substantially straight-chain aliphatic group ranging from 12–24 carbon atoms, the aliphatic group being capable of attracting and bonding, by means of van der Waals or hydrophobic forces, the undesired lipid present in the gastrointestinal tract for a time sufficient for the composition to be discharged from the gastrointestinal tract, and wherein the polymer is bonded to the aliphatic group by reacting the aliphatic group with the polymer at a ratio of 1–50% by weight of the aliphatic group relative to the polymer.

2. The method of claim 1 wherein the dosage ranges from about 0.1 gm/kg to 5.0 gm/kg body weight.

3. The method of claim 1 wherein said cellulosic polymer is selected from the group consisting of alpha cellulose, hydroxypropylmethyl cellulose, carboxymethyl cellulose, hydroxypropyl cellulose, hydroxyethyl cellulose and mixtures thereof.

4. The method of claim 1 wherein the undesired lipid is selected from cholesterol, cholesterol esters, fatty acids, fatty esters and derivatives thereof.

5. A method for effecting reduction of the biologically active level of an undesired lipid present in the fluid media of the gastrointestinal tract of humans or animals, said undesired lipid capable of being bound by a saturated or unsaturated alcohol, comprising:

orally administering therapeutically effective doses of a pharmaceutical composition containing a substantially water-soluble nondigestible polymer having multiple reactable hydroxyl groups, wherein said polymer is selected from the group consisting of the group consisting of cellulose polymers, algin, pectin, agar, chitin, polyvinyl alcohol and hydroxyethyl methacrylate, bonded through a biologically stable ether linkage to a saturated or unsaturated alcohol, the saturated or unsaturated alcohol being capable of attracting and bonding, by means of van der Waals or hydrophobic forces, the undesired lipid present in the gastrointestinal tract for a time sufficient for the composition to be discharged from the gastrointestinal tract, and wherein the polymer is bonded to the saturated or unsaturated alcohol by reacting the saturated or unsaturated alcohol with the polymer at a ratio of 1–50% by weight of the saturated or unsaturated alcohol relative to the polymer.

6. The method of claim 5 wherein the dosage ranges from about 0.1 gm/kg to 5.0 gm/kg body weight.

7. The method of claim 5 wherein said cellulosic polymer is selected from the group consisting of alpha cellulose, hydroxypropylmethyl cellulose, carboxymethyl cellulose, hydroxypropyl cellulose, hydroxyethyl cellulose and mixtures thereof.

8. The method of claim 5 wherein the undesired lipid is selected from the group consisting of cholesterol, cholesterol esters, fatty acids, fatty esters and derivatives thereof.

* * * * *